United States Patent [19]

Shimokobe et al.

[11] Patent Number: 4,524,824

[45] Date of Patent: Jun. 25, 1985

[54] DENTAL CEMENT

[75] Inventors: Hirokata Shimokobe, Sapporo; Sueo Saito, Tokyo; Kentaro Tomioka, Chofu; Shoji Akahane; Kazuo Hirota, both of Tokyo, all of Japan

[73] Assignee: G-C Dental Industrial Corporation, Tokyo, Japan

[21] Appl. No.: 484,517

[22] Filed: Apr. 13, 1983

[30] Foreign Application Priority Data

Apr. 20, 1982 [JP] Japan ................................. 57-64630

[51] Int. Cl.³ ............................................... C09K 3/00
[52] U.S. Cl. ........................................ 106/35; 433/228
[58] Field of Search ........................... 106/35; 433/228

[56] References Cited

U.S. PATENT DOCUMENTS 1,612,675 12/1926 Vivas .................................. 106/135

FOREIGN PATENT DOCUMENTS 1290627 9/1971 United Kingdom .

OTHER PUBLICATIONS

Kirk–Othmer Encyclopedia of Chemical Technology, third edition, vol. 7, (1979), pp. 463–468, (Herman F. Mark et al.).

Enzyklopadie der Technischen Chemie, 1922, (Fritz Ullmann), pp. 83, 90 and 91.

*Primary Examiner*—Theodore Morris
*Attorney, Agent, or Firm*—Oblon, Fisher, Spivak, McClelland & Maier

[57] ABSTRACT

A dental cement comprising a cement powder to which are added one or more of tannic acid derivatives consisting of the group of a tannic acid-protein combination, a tannic acid-formaldehyde combination, acetyl tannate and a metal salt of tannic acid, said tannic acid derivatives being sparingly soluble in water.

6 Claims, No Drawings

DENTAL CEMENT

FIELD OF THE INVENTION

The present invention generally relates to a dental cement and, more particularly, to a dental cement improved in solubility which relieves a patient from pain, when applied in his or her mouth for cementing or filling treatments.

BACKGROUND OF THE INVENTION

Many types of dental cements are currently on the market, and have very extensive applications. Typical examples of such cements are zinc phosphate cements obtained by the reaction of zinc oxide with phosphoric acid, carboxylate cements obtained by the reaction of zinc oxide with polycarboxylic acids, and glass ionomer cements obtained by the reaction of aluminosilicate glass with polycarboxylic acids. Other temporary filling and sealing cements are also available. Their primary use is cementing of crowns, inlays, bridges and orthodontic appliance, lining of various cavities and filling such cavity as class I, class III, or class V cavity. In general, these dental cements make use of chemical reactions between acids and bases. In most cases, the acidic components are supplied in the form of an aqueous solution due to their much solubility in water. In some cases, they may be powdered partly or wholly and blended in a cement powder. The basic components are ordinarily by far more difficult to dissolve in water than are the acidic components and, in most cases, are supplied in the powdery form. For use, the dental cements are mixed together to effect reaction between the acidic components and the basic components. Immediately upon mixing, the cement mixtures show considerably strong acidity, and usually change to neutrality with the lapse of time. Thus, the neutralization reaction of the cement mixtures are not yet completed in the initial stage where they are applied in the mouth of patients. To put it in another way, an appreciable amount of the acidic components remains in the cement mixtures. For this reason, when the cement mixture is close to the pulp of the tooth to be treated, the patient may suffer an unpleasant, or even acute, pain due to the strong irritating action of the remaining acids. In particular, the zinc phosphate, silicate and silicophosphate cements markedly hold their acidic irritating action owing to the use of an aqueous solution of phosphoric acid. Although the carboxylate or glass ionomer cements show relatively weaker acidic irritating action as compared with the zinc phosphate cements, yet that irritating action is by no means eliminated.

On the other hand, a major problem with the dental cements applied in the mouth is that they dissolve gradually in the saliva through many years. More specifically, when prosthetics such as crowns or inlays are cemented, a portion of cement filled in the gaps between the prosthesis and teeth dissolve with the lapse of time, resulting in the generating of secondary caries. When the dental cements are filled in the cavities, they start to dissolve from their surface with the resulting in deterioration of their appearance. For this reason, a reduction in the solubility of cement is an important problem to be solved.

In an effort of preparing a dental cement which is substantially free from any acidic irritating action and has a reduced solubility, it has unexpectedly been found that such a dental cement can be obtained by making use of a small amount of one or more of a tannic acid-protein combination, tannic acid-formaldehyde combination, acetyl tannic acid and a metal salt of tannic acid (hereinafter referred to as the tannic acid derivative(s)) which are difficult to dissolve in water. The dental cement according to the present invention is also found to be effective in relieving the pain during cementing.

DETAILED DESCRIPTION OF PREFERRED EMBODIMENTS OF THE INVENTION

The term "dental cement powder(s)" used in this specification refers to the powdery component of those used as the dental cements. More concretely, the powder consists mainly of a basic component, and usually contains a basic oxide. As already mentioned, the basic components may be mixed with a powdered acid component. For the composition of these dental cements, see, e.g., "Kirk-Othmer Encyclopedia of Chemical Technology" Third Edition, Vol. 7 (1979), pages 463–468 (Herman F. Mark et al).

It is well-known in the art that tannic acid is obtained from gallnuts, and it is astringent. However, although the addition of powdered tannic acid to cement powders helps reduce the acidic irritating action, yet soluble tannic acid gives rise to a color change tendency of cement. It has now been found, however, that the addition of sparingly soluble tannic acid derivatives such as protein combinations represses such a color change tendency, and is effective in improving the appearance of set dental cements. It has also turned out that the astringent effect of tannic acid can suffeciently be utilized in spite of the fact that such tannic acid derivatives are sparingly soluble in water.

The term "sparingly soluble tannic acid derivatives" used herein is understood to refer to those which dissolve slightly in water or are difficult to dissolve in water. Mentioned are particularly a tannic acid-protein combination, a tannic acid-formaldehyde combination, acetyl tannate and a metal salt of tannic acid. These combinations may be used alone or in admixture.

Proteins are generally the condensation polymer of amino acids. Either simple or conjugated proteins may be used for the present invention. For instance, we can use simple proteins such as protamine globulin, albumin, glutelin, prolamin and gelatin and conjugated proteins such as nuclear- and phospho-proteins. Among these proteins, particular preference is given to albumin and gelatin.

The metal salts of tannic acid used for the present invention are not critical. For example, use may be made of calcium, alminium, zinc, magnesium and strontiums salts of tannic acid. However, particular preference is given to the aluminium, zinc and calcium salts.

Preferably, 0.005–5% of weight of the tannic acid derivatives difficult to dissolve in water are added to cement powders. When the tannic acid derivatives are used in an amount below 0.005% by weight, neither reduction in solubility nor improvement in physical properties is obtained. Furthermore, any pain-relief effect is not substantially obtained. In an amount exceeding 5% by weight, the manipulation properties and strength of cement are decreased, and a reduction in solubility is not marked. In the present invention, the amount of the tannic acid derivatives is thus limited to a range of 0.005–5% by weight.

According to the present invention, the tannic acid derivatives can be applied to combinations other than a liquid-powder combination. In this case, they are not necessarily included in the powder component. For instance, with the paste type cement, the tannic acid derivatives may be added to the paste. Alternatively, with the hydraulic type cement, they may be added to the hydraulic cement powders. Thus, it is essential in the present invention that the tannic acid derivatives are added to any one of the cement compositions.

Besides the tannic acid derivatives, the dental cements according to the present invention may contain other additives known in the art.

For instance, the dental cements according to the present invention may contain astringent agents such as aluminium sulfate, potassium alum, bismuth gallate, zinc chloride, tannic acid, lactic acid, citric acid and the like to further relieve a patient from the pain during cementing.

The sparingly soluble tannic acid derivatives used in the present invention may be synthesized in various known manners. As a typical example, the synthesis of albumin tannate is explained.

Ten (10) grams of alubmin are dissolved in 500 cc of distilled water (Solution 1). Apart from this, twenty (20) grams of tannic acid are dissolved in 500 cc of distilled water (Solution 2). While stirring, Solutions 1 and 2 are mixed together to form precipitates. The precipitates are filtered out, washed with distilled water, and dried at 60° C. under a reduced pressure of 10 cm Hg to obtain the end product, albumin tannate.

Acetyl tannate and formaldehyde tannate may be prepared according to the manner as disclosed in "Enzyklopadie der Technischen Chemie", 1922, pages 83 and 91 (Fritz Ullmann).

The present invention will be explained in further detail with reference to the following non-restrictive examples wherein the tannic acid derivatives are incorporated into the cement powders.

EXAMPLE 1

0.1 g of albumin tannate and 99.9 g of glass ionomer cement powders (marketed from G-C Dental Industrial Corp. under the trade name of Fuji Ionomer, Type I, powder) were uniformly mixed together in a mortar. 1.4 grams of the thus obtained cement powders were blended with 1 gram of a glass ionomer cement setting liquid (marketed from G-C Dental Industrial Corp. under the trade name of Fuji Ionomer, type I, liquid) to obtain a dental cement mixture. The hardened dental cement was immersed in pure water for one day and measured on its solubility and crushing strength according to the testing method of JIS T 6602. The cement was found to have a solubility of 0.45% and a crushing strength of 1430 KG/cm$^2$. This dental glass ionomer cement is by far superior to the prior art cement (Table 1).

EXAMPLE 2

0.5, 1.0 and 2.0 grams of the albumin tannate used in the Example 1 were mixed with 99.9 g of the glass ionomer cement powders used in Example 1 in such a manner that the powders had a albumin tannate content of 0.5, 1.0 and 2.0 weight %. For the solubility and crushing strength of the thus obtained dental cements, see Table 1.

Comparative example 1 was effected wherein the tannate used in Example 1 was not applied.

From Table 1, the dental cements of Examples 1 and 2 are superior in solubility to those of comparative example 1.

TABLE 1

| No. | Albumin tannate content (%) | Solubility after one day (%) | Crushing strength after one day (Kg/cm$^2$) |
|---|---|---|---|
| 1 | 0.1 | 0.45 | 1430 |
| 2 | 0.5 | 0.3 | 1450 |
| 3 | 1.0 | 0.2 | 1480 |
| 4 | 2.0 | 0.2 | 1450 |
| Comparative example 1 | 0 | 0.6 | 1420 |

EXAMPLE 3

Aluminium tannate was mixed with dental zinc phosphate cement powders (marketed from G-C Dental Industrial Corp. under the trade name of Elite Cement 100, powder) in a concentration of 0.05, 0.1, 0.5, 1, 2 and 5 weight %. 1.45 grams of these cements were mixed with 0.5 ml of a dental zinc phosphate cement setting liquid (marketed from G-C Dental Industrial Corp. under the trade name of Elite Cement 100, liquid). The thus obtained dental cements were measured on their setting time, solubility and crushing strength according to JIS T 6602. The results are set forth in Table 2.

Comparative example 2 was effected wherein the aluminium tannate was not used.

From Table 2, it is found that the dental cements of Ex. 3 show a solubility lower than those of comparative example 2, and are best suited for dental purposes.

TABLE 2

| No. | Aluminium Tannate content (%) | Setting Time (m.n., sec.) | Solubility (%) | Crushing strength (Kg/cm$^2$) |
|---|---|---|---|---|
| 1 | 0.05 | 7'00" | 0.03 | 1505 |
| 2 | 0.1 | 7'00" | 0.02 | 1510 |
| 3 | 0.5 | 7'00" | 0.01 | 1540 |
| 4 | 1.0 | 7'00" | 0.01 | 1550 |
| 5 | 2.0 | 7'15" | 0.01 | 1530 |
| 6 | 5.0 | 7'15" | 0.01 | 1515 |
| Comparative example 2 | 0 | 7'00" | 0.03 | 1500 |

EXAMPLE 4

0.1, 0.5, 1 and 3% by weight of zinc tannate were further added to the cement powders containing 0.5% by weight of albumin tannate as described in Example 2. Table 3 shows the solubility and crushing strength of the resulting dental cements.

These dental cements have much superior properties as compared with those of the prior art cement.

TABLE 3

| No. | Zinc tannate content (%) | Solubility after one day (%) | Crushing strength after one day (kg/cm$^2$) |
|---|---|---|---|
| 1 | 0.1 | 0.3 | 1460 |
| 2 | 0.5 | 0.2 | 1490 |
| 3 | 1.0 | 0.2 | 1470 |
| 4 | 3.0 | 0.2 | 1450 |

EXAMPLE ON PAIN-RELIEF EFFECT 1 gram of acetyl tannate and 99 grams of carboxylate cement powders (marketed from G-C Dental Industrial Corp. under the trade name of Carbolit 100, powder) were sufficiently mixed together to obtain cement powders. These powders were mixed with a carboxylate cement setting liquid (marketed from G-C Dental Industrial Corp. under the trade name of Carbolit 100, liquid) in a powder-liquid ratio of 1.7:1.0 g. The thus obtained dental cement was used for cementing of metal crowns or inlays. The crowns treated were the first or second molars of the lower jaws. By radiography, the distance between the cement layer and the pulps was found to be 0.5–0.7 mm. A total of 32 cases were examined. The pain the patients suffered was broken down into four grades, none, slight, unpleasant and acute. A total of 15 control cases were also examined wherein no acetyl tannate was used. The results are given in Table 4.

TABLE 4

| Degree of irritation | Invention | Prior Art |
| --- | --- | --- |
| Acute | 0 | 1 |
| Unpleasant | 0 | 6 |
| Slight | 4 | 8 |
| None | 28 | 0 |

What is claimed is:

1. A dental cement powder composition comprising a dental cement powder and 0.005–5 percent by weight of one or more of tannic acid derivatives selected from the group consisting of a tannic acid-protein combination, a tannic acid-formaldehyde combination, acetyl tannate and a metal salt of tannic acid, said tannic acid derivatives being sparingly soluble in water, said tannic acid derivative being present in amount sufficient to reduce the solubility of the dental cement formed with the dental cement powder, wherein the dental cement powder is the powder of a dental cement which is a zinc phosphate cement, a polycarboxylate cement prepared from the reaction of a basic component and a polycarboxylic acid or a glass ionomer cement.

2. A dental cement powder composition as recited in claim 1, in which said tannic acid derivative is albumin tannate.

3. A dental cement powder composition as recited in claim 1, in which said tannic acid derivative is gelatin tannate.

4. A dental cement as recited in claim 1, in which said tannic acid derivative is aluminum tannate.

5. A dental cement as recited in claim 1, in which said tannic acid derivative is zinc tannate.

6. A dental cement as recited in claim 1, in which said tannic acid derivative is calcium tannate.

* * * * *